United States Patent [19]

Tsunoda et al.

[11] 4,396,551

[45] Aug. 2, 1983

[54] METHOD FOR THE RECOVERY OF GROUP VIII NOBLE METAL SOLID COMPLEXES

[75] Inventors: Yoshitoshi Tsunoda, Komae; Shimpei Tomita; Chihiro Miyazawa, both of Kurashiki; Yasuro Omori, Okayama, all of Japan

[73] Assignee: Mitsubishi Chemical Industries Ltd., Tokyo, Japan

[21] Appl. No.: 314,343

[22] Filed: Oct. 23, 1981

[30] Foreign Application Priority Data

Oct. 23, 1980 [JP] Japan ............................ 55-148824

[51] Int. Cl.$^3$ ............................................. C07F 15/00
[52] U.S. Cl. ........................... 260/429 R; 252/411 R; 252/416; 252/417
[58] Field of Search ............... 260/429 R; 252/411 R, 252/416, 417, 419

[56] References Cited

U.S. PATENT DOCUMENTS

| | | | |
|---|---|---|---|
| 3,102,899 | 9/1963 | Cannell | 260/439 R |
| 3,547,964 | 12/1970 | Olivier | 260/429 R |
| 3,641,076 | 2/1972 | Booth | 260/429 R |
| 3,755,393 | 8/1973 | Kniese et al. | 260/429 R X |
| 3,968,134 | 7/1976 | Gregorio et al. | 260/429 R |
| 4,135,911 | 1/1979 | Balmat | 252/411 R X |
| 4,224,235 | 9/1980 | Beisner et al. | 252/411 R X |
| 4,225,530 | 9/1980 | Beisner et al. | 252/411 R X |
| 4,260,518 | 4/1981 | Katzer et al. | 252/411 S |

OTHER PUBLICATIONS

Gregorio et al, Inorganica Chemica Acta, pp. 89–93 (1969).

Ahmad et al, J. of the Chemical Society, Dalton Transactions, pp. 843–847 (1972).

Primary Examiner—Helen M. S. Sneed
Attorney, Agent, or Firm—Sughrue, Mion, Zinn, Macpeak and Seas

[57] ABSTRACT

A method for the recovery of a Group VIII noble metal solid complex is described, which comprises bringing an organic compound-containing solution containing therein a Group VIII noble metal complex having a tertiary organophosphorous compound as a ligand into contact with an oxidizing agent in the presence of a free tertiary organophosphorous compound, an organic polar solvent, water, and a basic substance to preciptate a solid complex of the Group VIII noble metal, and a separating the precipitated Group VIII noble metal solid complex from the solution.

13 Claims, No Drawings

METHOD FOR THE RECOVERY OF GROUP VIII NOBLE METAL SOLID COMPLEXES

FIELD OF THE INVENTION

The present invention relates to a method for the recovery of Group VIII noble metal solid complexes. More particularly, it is concerned with a method for the economical and efficient recovery of Group VIII noble metal solid complexes from organic compound-containing solutions containing therein complexes of Group VIII noble metals and tertiary organophosphorous compound ligands.

BACKGROUND OF THE INVENTION

Complexes comprising Group VIII noble metals and tertiary organophosphorus compounds are useful for various homogeneous catalytic reactions such as hydrogenation of olefins, carbonyl compounds, aromatic compounds, and the like, and hydroformylation and hydrocarboxylation of olefins. In particular, rhodium-triarylphosphine complexes are commercially advantageously used as catalysts for the hydroformylation of olefins.

These Group VIII noble metal complexes have advantages because of the excellent chemical stability thereof in that a catalyst liquid can be separated from a reaction product by distillation, returned to a reaction zone, and reused, and in that the reaction can be performed continuously while separating the reaction product by distilling away from the reaction zone by gas stripping and allowing the catalyst liquid to remain in the reaction zone. In these reactions, however, various high boiling by-products are formed and the deactivation of catalyst occurs. In carrying out these reactions continuously, therefore, it is necessary to extract a portion of the catalyst liquid continuously or intermittently from the reaction zone since such high boiling by-products and deactivated catalyst accumulate therein.

The thus-extracted catalyst liquid contains expensive Group VIII nobel metals and, therefore, it is very important to efficiently recover such noble metals from an economical viewpoint and furthermore, from a viewpoint of prevention of environmental pollution. In recovering Group VIII noble metals from the extracted catalyst liquid, it is desirable to recover them in the form of a complex which is active for the above-described reactions.

Heretofore known methods of separating and recovering Group VIII noble metal complexes from extracted catalyst liquids include an extraction with a strong acid as described in Japanese Pat. Publication No. 43219/71, and a decomposition with a peroxide compound as described in U.S. Pat. No. 3,547,964 and Japanese Laid-Open Patent Application (OPI) No. 63388/76.

The extraction with a strong acid is a method of recovering a rhodium complex in which a strong acid (for example, 60% by weight or more sulfuric acid) is added to a spent catalyst liquid to extract the rhodium complex therewith, the resulting acid solution containing the rhodium complex, which is separated by phase-separation, is diluted with water to precipitate the rhodium complex, and the precipitate is extracted with a solvent to recover the rhodium complex from the acid solution.

The decomposition method using a peroxide compound comprises treating a spent catalyst liquid with an aqueous solution of an acid, such as nitric acid, and a peroxide compound, isolating the aqueous phase containing a rhodium salt, and after the decomposition with heating of excessive peroxide compound, treating the aqueous phase with carbon monoxide under pressure in the presence of an organic solvent and a complex-forming substance, such as triphenylphosphine, to thereby obtain the rhodium complex in the organic solvent phase.

In either of the above-described methods, the problem of corrosion of apparatus material arises since they use an acid. Furthermore, since the recovered rhodium complex contains sulfate ions ($SO_4^{2-}$) and chloride ions ($Cl^-$), and the sulfur (S) and chlorine (Cl) poison the rhodium complex catalyst, it is necessary to remove them by neutralizing with an alkali.

Japanese Laid-Open patent application (OPI) No. 26218/79 discloses a method in which a still residue of a hydroformylation reaction solution containing therein a rhodium-triarylphosphite complex catalyst is subjected to a pretreatment along with a compatible organic solvent, water, oxygen gas, and a base, heated at 0° to 85° C. until the triarylphosphite is oxidized into a phosphate, and then heated at 115° to 175° C. to thereby precipitate zero valent rhodium, and additionally, a method in which the thus-obtained rhodium precipitate is converted into rhodium oxide ($Rh_2O_3$) by application of a procedure of several steps.

This method, however, has disadvantages in that it is very difficult to convert the precipitate of zero valent rhodium, i.e., rhodium in the form of a metal, into a rhodium complex having catalytic activity, and in that the rhodium oxide obtained by application of the above complicated procedure requires a treatment with carbon monoxide and triarylphosphite at high temperature and pressure for the formation of a complex thereof.

As a result of extensive investigations to develop a method of recovering Group VIII noble metal complexes in an organic compound-containing solution efficiently by a simplified method and, furthermore, as a complex which is active for the above-described reactions, it has been found that when the foregoing solution is brought into contact with an oxidizing agent in the presence of a tertiary organophosphorous compound, an organic polar solvent, water and a basic substance, solid complexes of Group VIII noble metals are precipitated.

SUMMARY OF THE INVENTION

An object of the invention is to provide a method for commercially advantageously separating and recovering solid complexes of Group VIII noble metals from an organic compound-containing solution containing therein Group VIII noble metal complexes.

Another object of the invention is to provide a method for commercially advantageously separating and recovering Group VIII noble metals from an extracted catalyst liquid for the commercially advantageous practice of hydroformylation of olefins.

A further object of the invention is to provide a method for separating and recovering selectively a rhodium-triarylphosphine complex having sufficient catalytic activity for hydroformylation in the form of a solid complex from an extracted catalyst liquid obtained from a hydroformylation reaction solution containing a rhodium-triarylphosphine complex, free triarylphosphine, and high boiling by-products.

The present invention, therefore, provides a method of recovering a Group VIII noble metal solid complex which comprises bringing an organic compound-containing solution containing therein a Group VIII noble metal complex having a tertiary organophosphorous compound as a ligand into contact with an oxidizing agent in the presence of a free tertiary organophosphorous compound, an organic polar solvent, water and a basic substance to precipitate a solid complex of the Group VIII noble metal, and separating the precipitated Group VIII noble metal solid complex from the solution.

DETAILED DESCRIPTION OF THE INVENTION

The method of the invention is applied to the recovery of a Group VIII noble metal in the form of a complex from an organic compound-containing solution containing therein a Group VIII noble metal complex having at least one tertiary organophosphorous compound as a ligand. In particular, the method of the invention is advantageously used for the recovery of a Group VIII noble metal contained in a catalyst liquid, which is separated from reaction products by, for example, distillation in the hydroformylation, hydrocarboxylation or the like of olefinic compounds, as a complex thereof.

Group VIII noble metal complexes having tertiary organophosphorous compounds as ligands can be easily prepared from Group VIII noble metal compounds, such as hydrides, halides, carboxylates, nitrates, and sulfates, and tertiary organophosphorous compounds, such as tertiary phosphines and tri-substituted phosphites, by a known complex-forming method. In some cases, Group VIII noble metal compounds and tertiary organophosphorous compounds can be introduced into a reaction system to thereby form complexes therein.

Group VIII noble metal compounds which can be used in the preparation of complexes include ruthenium compounds, e.g., ruthenium trichloride, and tetraaminehydroxochloro-ruthenium chloride; rhodium compounds, e.g., rhodium dicarbonylchloride, rhodium nitrate, rhodium trichloride, rhodium acetate, and rhodium sulfate; palladium compounds, e.g., palladium hydride, palladium chloride, palladium cyanide, palladium iodide, palladium nitrate, palladium acetate, and palladium sulfate; osmium compounds, e.g., osmium trichloride and chloroosmic acid; iridium compounds, e.g., iridium tribromide, iridium tetrabromide, iridium trifluoride, iridium trichloride, and iridium carbonyl; and platinum compounds, e.g., platinic acid, platinous iodide, sodium hexachloroplatinate, and potassium trichloro(ethylene)platinate.

Tertiary organophosphorous compounds which can be used in the preparation of complexes include tertiary phosphines, e.g., trimethylphosphine, tris(aminoamyl)phosphine, tricyclohexylphosphine, triphenylphosphine, tris(N,N-dimethylanilyl)phosphine, tri-p-tolylphosphine, tri-m-tolylphosphine, phenyldiisopropylphosphine, phenyldiamylphosphine, ethyldiphenylphosphine, tris(N,N-diethylaminomethyl)phosphine, ethylenebis(diphenylphosphine), trianilylphosphine, diphenyl(N,N-dimethylanilyl)phosphine, triphenylanilylethylenediphosphine, tris(3,5-diaminophenyl)phosphine, and aminoethyltriisopropylhexamethylenediphosphine; and tri-substituted phosphites, e.g., trimethylphosphite, triphenylphosphite, tricyclohexylphosphite, and tetraphenylethylenediphosphite.

Hereinafter, the invention will be explained in detail with reference to a method of separating and recovering a Group VIII noble metal solid complex from a catalyst liquid used in a hydroformylation reaction in which a Group VIII noble metal complex prepared from a Group VIII noble metal compound and a tertiary organophosphorous compound as described hereinbefore, particularly a rhodium-triarylphosphine complex is used as a catalyst.

The hydroformylation reaction is carried out by reacting an olefinic compound containing 2 to 20 carbon atoms, such as straight $\alpha$-olefins, e.g., ethylene, propylene, 1-butene, 1-hexene, and 1-octene, and olefins having a vinylidene structure, e.g., isobutene, with oxo gas consisting of carbon monoxide and hydrogen ($H_2/CO$ (molar ratio) = 1:3 to 20:1) in the presence of the rhodium-triarylphosphine complex under the conditions of a pressure of 1 to 100 atmospheric pressure and a temperature of 50° to 200° C. in the presence or absence of a solvent.

The concentration of the rhodium complex in the reaction medium is usually several milligrams to several hundred milligrams per liter as calculated as a rhodium atom. The triarylphosphine as used as a ligand is present in the reaction medium in an excessive amount of several mols to several thousand mols per mol of the rhodium complex catalyst in order to increase the stability of the catalyst.

Aldehyde formed by the hydroformylation reaction is separated and recovered from the catalyst liquid by stripping with unreacted gases, distillation, or like technique. The catalyst liquid is reused for the reaction either by being allowed to remain in the reaction zone, or by being recycled to the reaction zone. A part of the catalyst liquid is withdrawn continuously or intermittently as a spent catalyst liquid from the reaction zone in order to prevent accumulation of deactivated catalyst or in some cases, by-produced high boiling by-products. In an amount corresponding to the amount withdrawn, a fresh catalyst and triarylphosphine are introduced into the reaction zone.

The method of the invention is preferably applied to the spent catalyst liquid withdrawn from the reaction zone. However, when the spent catalyst liquid contains a large amount of reaction solvent in addition to high boiling by-products, it is preferred to apply the method of the invention after the concentration of the complex catalyst in the spent catalyst liquid is increased usually to 10 mg/l or more, preferably 100 mg/l or more, and most preferably 500 mg/l or more as calculated as a rhodium atom by removing the reaction solvent from the spent catalyst liquid by a known method such as distillation.

In accordance with the method of the invention, an organic compound-containing solution containing therein a Group VIII noble metal complex having at least one tertiary organophosphorous compound as a ligand is brought into contact with an oxidizing agent in the presence of a free tertiary organophosphorous compound, an organic polar solvent, water and a basic substance to thereby precipitate a solid complex of the Group VIII noble metal.

The amount of the free tertiary organophosphorous compound being present in the organic compound-containing solution is one mol or more and preferably 10 mols or more per mol of the Group VIII noble metal. When the tertiary organophosphorous compound is not present in the organic compound-containing solution, the Group VIII noble metal is precipitated not as a solid complex but as a zero valent metal on being brought into contact with the oxidizing agent.

Preferred examples of organic polar solvents which are present in the organic compound-containing solution are alcohols and mixtures of such alcohols and organic solvents which become poor solvents for the precipitated solid complex. Alcohols which can be used include monohydric and dihydric alcohols containing 1 to 12 carbon atoms, such as ethyl alcohol, n-propyl alcohol, isopropyl alcohol, tert-butyl alcohol, ethylene glycol monomethyl ether, ethylene glycol monoethyl ether, and ethylene glycol. These alcohols can be used alone or in combination with each other.

As poor solvents for the precipitated solid complex, there can be mentioned those solvents in which the Group VIII noble metal-tertiary organophosphorous compound complex is sparingly soluble, such as ethers containing 2 to 12 carbon atoms, e.g., dimethyl ether and diethyl ether, and paraffins containing 5 to 10 carbon atoms, e.g., n-pentane, n-hexane, and n-heptane.

Of the foregoing organic polar solvents, ethyl alcohol, isopropyl alcohol, n-propyl alcohol, ethylene glycol monomethyl ether and ethylene glycol monoethyl ether are preferred, and ethyl alcohol, isopropyl alcohol and n-propyl alcohol are particularly preferred.

The organic polar solvent is added in an amount enough to make the resulting solution a poor solvent system for the precipitating solid complex, said amount being dependent on the amount of water present. In the case of alcohols, it is desired that the alcohol is present in an amount of 1 mol or more per mol of the Group VIII noble metal. The preferred amount of the organic polar solvent being added varies depending on the type and amount of the reaction solvent and high boiling by-products contained in the organic compound-containing solution. When the amount of the organic polar solvent being added is too small, the recovery of the Group VIII noble metal solid complex is reduced.

The amount of water present in the organic compound-containing solution is 1 mol or more per mol of the Group VIII noble metal. Water may be added either as it is or in the form of an aqueous solution of the basic substance.

Basic substances which can be used include hydroxides of alkali metals and alkaline earth metals, such as sodium hydroxide, potassium hydroxide, and calcium hydroxide; amines, such as isobutylamine and n-butylamine; and ammonia. The amount of the basic substance being added is determined so that after the precipitation of the Group VIII noble metal solid complex by contacting the organic compound-containing solution with the oxidizing agent in the presence of the tertiary organophosphorous compound, organic polar solvent, and water, the resulting solution becomes alkaline and preferably the pH of the solution is 8 or more. In particular, when the organic compound-containing solution contains acidic substances, or precursors, such as esters, which undergo such reactions as hydrolysis on addition of basic substances, forming acidic substances, the basic substance is consumed by the acidic substance and, therefore, it is necessary to control the amount of the basic substance being added taking into account the consumption amount of the basic substance due to the acidic substance.

Oxidizing agents which can be used for contacting with the organic compound-containing solution include oxygen gas, oxygen gas-containing substances, e.g., air, inorganic peroxides, e.g., hydrogen peroxide, and organic peroxides, e.g., benzoyl peroxide. Air is commercially advantageously used. The amount of the oxidizing agent being added is required to be 1 mol or more per mol of the Group VIII noble metal. When air is used as an oxidizing agent, it is sufficient to keep the solution system in an atmosphere of air. However, air may be bubbled through the solution, or may be used under pressure.

The conditions under which the organic compound-containing solution is contacted with the oxidizing agent are required to be such that there is present a tertiary organophosphorous compound in free form in the solution system during the contact treatment and after the precipitation of the Group VIII noble metal solid complex by the contact treatment. Usually, when a mixture of the organic compound-containing solution, tertiary organophosphorous compound, organic polar solvent, water and basic substance is brought into contact with the oxidizing agent at a temperature of 0° to 150° C. for a period of several minutes to several days and preferably at a temperature of 30° C. to the boiling point of the solution system for a period of several minutes to several hours, the Group VIII noble metal solid complex having the tertiary organophosphorous compound as a ligand can be precipitated. The amount of the Group VIII noble metal solid complex being precipitated can be increased by further lowering the temperature of the solution system containing the precipitating Group VIII noble metal solid complex.

The chemical structure of the precipitated Group VIII noble metal solid complex varies depending on the type of the Group VIII noble metal, and type of the tertiary organophosphorous compound, and the composition of the treatment solution, for example, the presence of coordinate compounds other than the tertiary organophosphorous compounds. For example, when a catalyst liquid of a hydroformylation reaction in which a rhodiumtriarylphosphine compex is used as a catalyst is contacted with an oxidizing agent in the presence of triarylphosphine, alcohols, water and a basic substance, a rhodium complex composed mainly of a complex represented by the general formula: $HRh(PAr_3)_n$ (wherein Ar is an aryl group, and n is an integer of 1 to 4) is precipiated.

The precipitated Group VIII noble metal solid complex is subjected to solid-liquid separation by the usual solid-liquid separation method, e.g., filtration, centrifugal filtration, and centrifugal separation, whereby the Group VIII noble metal solid complex is separated and recovered.

The thus-separated and recovered Group VIII noble metal solid complex has a catalytic activity sufficient to carry out a hydroformylation or hydrocarboxylation reaction. The Group VIII noble metal solid complex, therefore, can be recycled to a hydroformylation or hydrocarboxylation reaction zone and reused as a catalyst as it is or after the removal of basic substances by the known method, e.g., water-washing.

As described above in detail, the method of the invention permits to efficiently recover a Group VIII noble metal solid complex having a tertiary organophosphorous compound as a ligand from an organic compound-containing solution by a simple procedure, and furthermore, the recovered Group VIII noble metal solid complex can be recycled to a hydroformylation or hydrocarboxylation reaction zone and reused as it is since it has an enough catalytic activity. Thus, the commerical value of the invention is very great.

Hereinafter, the invention is described in greater detail with reference to the following examples although it is not limited thereto.

EXAMPLE 1

A spent catalyst liquid resulting from the hydroformylation of propylene with a rhodium-triphenylphosphine complex catalyst was concentrated by distillation to adjust the concentration of the complex as calculated as a rhodium atom to 800 mg/l and the concentration of free triphenylphosphine to 570 mmol/l. Then, 100 ml of the resulting high boiling medium liquid was introduced into a 1,000-ml four-necked flask equipped with a reflux condenser, a thermometer, and a stirring device, and heated up to 70° C. while stirring. Subsequently, 100 ml of a 20% by weight aqueous solution of sodium hydroxide and 400 ml of ethyl alcohol were added thereto, and the resulting mixture was treated in an atmosphere of air under ordinary pressure at 70° C. After about 20 minutes, a rhodium complex began to precipitate. After the treatment was performed for 5 hours, the precipitate was filtered under pressure, washed with water and ethyl alcohol, and vacuum-dried at room temperature to thereby obtain a bright golden yellow solid complex.

The thus-obtained solid complex contained 8% by weight of rhodium and 10% by weight of phosphorus. Infrared ray absorption spectral analysis by the nujol method of the solid complex showed an absorption at 2149 $cm^{-1}$ which was believed to be ascribed to the Rh-H bond. Furthermore, it was found that absorption peaks at 400 $cm^{-1}$ to 4000 $cm^{-1}$ were substantially in agreement with those of hydridotetraquis(triphenylphosphine)rhodium $\{HRh[P(C_6H_5)_3]_4\}$ as described in Journal of the American Chemical Society, page 3013, May 20, 1970. On the basis of the foregoing data, it is assumed that the solid complex has mainly the chemical formula of $HRh[P(C_6H_5)_3]_{3-4}$.

The recovery of the rhodium complex was 80% as calculated as a rhodium atom. With the solution just after the start of the treatment, and the filtrate after the filtration, the pH was measured with a pH test paper, and it was found that in either case the pH was 11 or more. The concentration of triphenylphosphine in the filtrate after the filtration was 50 mmol/l, and it can be seen that 45 mmol/l of triphenylphosphine (the concentration before the treatment: 90 mmol/l) was oxidized into triphenylphosphine oxide.

EXAMPLE 2

The procedure of Example 1 was repeated with the exception that n-propyl alcohol was used in place of ethyl alcohol.

The recovery of the rhodium complex was 70%. The pH of the solution just after the treatment, and the pH of the filtrate after the filtration as determined with a pH test paper were 11 or more. The concentration of triphenylphosphine in the filtrate after the filtration was 60 mmol/l, and it can be seen that 35 mmol/l of triphenylphosphine (the concentration before the treatment: 95 mmol/l) was oxidized into triphenylphosphine oxide.

EXAMPLE 3

The procedure of Example 1 was repeated with the exception that ethylene glycol monomethyl ether was used in place of ethyl alcohol.

The recovery of the rhodium complex was 40%. The pH of the solution just after the treatment, and the pH of the filtrate after the filtration as determined with a pH test paper were 11 or more. The concentration of triphenylphosphine in the filtrate after the filtration was 60 mmol/l, and it can be seen that 35 mmol/l of triphenylphosphine (the concentration before the treatment: 95 mmol/l) was oxidized into triphenylphosphine oxide.

EXAMPLE 4

The procedure of Example 1 was repeated with the exception that ethylene glycol monoethyl ether was used in place of ethyl alcohol.

The recovery of the rhodium complex was 33%. The pH of the solution just after the treatment, and the pH of the filtrate after the filtration as determined with a pH test paper were 11 or more. The concentration of triphenylphosphine in the filtrate after the filtration was 60 mmol/l, and it can be seen that 35 mmol/l of triphenylphosphine (the concentration before the treatment: 95 mmol/l) was oxidized into triphenylphosphine oxide.

COMPARATIVE EXAMPLE 1

The procedure of Example 1 was repeated with the exception that all the steps were performed in an atmosphere of nitrogen. Even after the treatment was performed for 5 hours, no rhodium complex was precipitated.

COMPARATIVE EXAMPLE 2

The same high boiling medium liquid as used in Example 1 was used, and the triphenylphosphine contained in the liquid was oxidized with air at 70° C. to adjust the concentration of free triphenylphosphine to 3 mmol/l. The thus-prepared liquid was subjected to the same procedure as in Example 1 whereupon rhodium in metallic form was precipitated. The concentration of triphenylphosphine in the liquid was 0 mmol/l.

COMPARATIVE EXAMPLE 3

When the procedure of Example 1 was repeated with the exception that 100 ml of a 0.3% by weight aqueous solution of sodium hydroxide was used in place of a 20% by weight aqueous solution of sodium hydroxide, no rhodium complex was precipitated. The pH of the treatment solution was within the range of 2 to 5. The concentration of triphenylphosphine in the solution was 55 mmol/l, and it can be seen that 40 mmol/l of triphenylphosphine (the concentration before the treatment: 95 mmol/l) was oxidized into triphenylphosphine oxide.

REFERENCE EXAMPLE 1

In order to examine the activity of a recovered rhodium complex for hydroformylation of olefins, the following experiment was conducted.

The rhodium complex recovered in Example 1 was dissolved in a toluene solution containing 10% by weight of triphenylphosphine so that the concentration of the rhodium complex as calculated as a rhodium atom becomes 100 mg/l. Hereinafter, this sodium is referred to as Catalyst Liquid A.

A 200-ml autoclave equipped with a magnetic stirrer was charged with 50 ml of Catalyst Liquid A and 10 g of propylene. A mixed gas of hydrogen and carbon monoxide (oxo gas, $H_2/CO=1:1$ (molar ratio)) was introduced into the autoclave under pressure at a temperature of 120° C., and reaction was started while maintaining the reaction pressure at 50 kg/cm$^2$G. In order to maintain the pressure at the constant level during the reaction, the autoclave was connected to a high pressure gas holder through a pressure controller, and the oxo gas consumed by the reaction was supplemented. Presuming that the reaction was completed when no gas absorption was observed (after 3 hours), the autoclave was cooled and, therefore, residual propylene and formed butyraldehyde in gas and liquid phases were analyzed by gas chromatography.

As a result, it was found that the conversion of propylene was 99%, and the selectivity of butyraldehyde was 99%. The rate constant (apparent first-order reaction) as determined by a reduction curve of the oxo gas pressure in the high pressure gas holder was 6.0 (l/Hr).

For comparison, the same procedure as described above was repeated with the exception that hydridocarbonyltris(triphenylphosphine)rhodium prepared from rhodium trichloride ($RhCl_3.3H_2O$) by the usual method was used as a catalyst. The conversion of propylene was 99.1%, and the selectivity of butyraldehyde was 98%. The rate constant (apparent first-order reaction) was 6.2 (l/Hr).

As can be seen from the foregoing results, the rhodium complex recovered by the method of the invention has enough activity for hydroformylation of olefins. It was thus confirmed that even if the recovered rhodium complex was recycled as it is to the hydroformylation reaction zone and reused, the desired reaction results (conversion and selectivity) and reaction rate could be obtained. Of course, it is apparent that the recovered rhodium complex may be subjected to any suitable purification treatment.

While the invention has been described in detail and with reference to specific embodiments thereof, it will be apparent to one skilled in the art that various changes and modifications can be made therein without departing from the spirit and scope thereof.

What is claimed is:

1. A method for separating and recovering a Group VIII noble metal solid complex which comprises bringing a solution containing a catalyst for hydroformylation containing therein a Group VIII noble metal complex having a tertiary organophosphorous compound as a ligand into contact with an oxidizing agent in the presence of a free tertiary organophosphorous compound, an organic polar solvent, water and a basic substance to precipitate a solid complex of the Group VIII noble metal, and separating the precipitated Group VIII noble metal solid complex from the solution.

2. The method as claimed in claim 1, wherein the solution containing a catalyst for hydroformylation is an extracted catalyst liquid obtained from a hydroformylation reaction solution.

3. The method as claimed in claim 1 wherein the Group VIII noble metal is rhodium.

4. The method as claimed in claim 1 or 3, wherein the tertiary organophosphorous compound is triarylphosphine.

5. The method as claimed in claim 4, wherein the tertiary organophosphorous compound is triphenylphosphine.

6. The method as claimed in any of claims 1, 3 to 5, wherein the amount of the basic substance present in the solution containing a catalyst for hydroformylation is such that it is sufficient to keep the solution after the precipitation of the Group VIII noble metal solid complex at pH 8 or more.

7. The method as claimed in any of claims 1, 3 to 6, wherein the organic polar solvent is a monohydric alcohol containing 1 to 12 carbon atoms.

8. The method as claimed in claim 7, wherein the organic polar solvent is ethyl alcohol.

9. The method as claimed in claim 7, wherein the organic polar solvent is propyl alcohols.

10. The method as claimed in any of claims 1, 3 to 6, wherein the organic polar solvent is a dihydric alcohol containing 1 to 12 carbon atoms.

11. The method as claimed in any of claims 1, 3 to 10, wherein the basic substance is a hydroxide of an alkali metal or alkaline earth metal.

12. The method as claimed in any of claims 1, 3 to 11, wherein the temperature of the treatment to precipitate the Group VIII nobel metal solid complex is 0° to 150° C.

13. The method as claimed in any of claims 1, 3 to 12, wherein the oxidizing agent is an oxygen gas-containing substance.

* * * * *